(12) United States Patent
Oki et al.

(10) Patent No.: US 12,140,527 B2
(45) Date of Patent: Nov. 12, 2024

(54) CORROSION AMOUNT ESTIMATION DEVICE AND CORROSION AMOUNT ESTIMATION METHOD

(71) Applicant: Nippon Telegraph and Telephone Corporation, Tokyo (JP)

(72) Inventors: Shota Oki, Musashino (JP); Shingo Mineta, Musashino (JP); Mamoru Mizunuma, Musashino (JP); Soichi Oka, Musashino (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 823 days.

(21) Appl. No.: 17/057,575

(22) PCT Filed: May 20, 2019

(86) PCT No.: PCT/JP2019/020328
§ 371 (c)(1),
(2) Date: Nov. 20, 2020

(87) PCT Pub. No.: WO2019/225664
PCT Pub. Date: Nov. 28, 2019

(65) Prior Publication Data
US 2021/0199561 A1    Jul. 1, 2021

(30) Foreign Application Priority Data

May 23, 2018   (JP) .................................. 2018-098549

(51) Int. Cl.
*G01N 17/02* (2006.01)
*G01N 27/26* (2006.01)
*G01N 33/24* (2006.01)

(52) U.S. Cl.
CPC ............. *G01N 17/02* (2013.01); *G01N 27/26* (2013.01); *G01N 33/24* (2013.01)

(58) Field of Classification Search
None
See application file for complete search history.

(56) References Cited

PUBLICATIONS

International Search Report dated Aug. 27, 2019, issued in PCT Application No. PCT/JP2019/020328, filed May 22, 2019.
(Continued)

*Primary Examiner* — J. Christopher Ball
(74) *Attorney, Agent, or Firm* — Workman Nydegger

(57) ABSTRACT

A corrosion amount estimation apparatus includes a soil analysis unit adapted to acquire a particle diameter distribution in soil in each of plural soil samples; a corrosion measurement unit adapted to take electrochemical measurements at plural soil moisture percentage values on an electrode containing the metallic material buried in each of the soil samples; a soil classification unit adapted to classify the soil in each of the soil samples; a corrosion rate calculation unit adapted to calculate a corrosion rate regarding each of the soil samples at each of the soil moisture percentage values and identify a local maximum corrosion rate; a corrosion estimation curve generation unit adapted to generate a corrosion estimation curve; and a corrosion amount estimation unit adapted to acquire the class proportions of actual soil in which the metallic material is buried, acquire the local maximum corrosion rate corresponding to the class proportions from the corrosion estimation curve, and estimate the corrosion amount of the metallic material.

2 Claims, 11 Drawing Sheets

(56) References Cited

PUBLICATIONS

Kiyoshi Kaito et al., *The Effects of Prior Subjective Information to Bayesian Updating Results of Determination Prediction*, Structural Engineering Thesis, vol. 53A, May 2007, pp. 774-783.

Bunzo Tsujino et al., *Corrosion Behavior of Steel and Application of Monitoring in Soil*, Surface Technology, vol. 40, No. 5, 1989, pp. 707-708.

Satoru Yamamoto et al., *Development of Corrosion Rate Measurement Method for Steel in Concrete (CIPE Method)*, Rust, No. 148, 2015, pp. 2-7.

Giichi Miyata et al., *Corrosion Monitoring of Metals in Soils by Electrochemical and Related Methods: Part I*, Zairyo-to-Kankyo, vol. 46, No., 9, 1997, pp. 541-551.

CORROSION AMOUNT ESTIMATION DEVICE AND CORROSION AMOUNT ESTIMATION METHOD

TECHNICAL FIELD

The present invention relates to a technique for estimating a corrosion amount of metallic materials buried underground.

BACKGROUND ART

Infrastructure equipment supporting our lives has been developed in quantity rapidly in approximately 20 years during and after the period of high economic growth. Consequently, in 2030, equipment constructed more than 50 years ago will makes up a majority, and there is concern that aging equipment is expected to increase more and more from now on. Also, the workforce of skilled technicians essential in ensuring proper maintenance and management of infrastructure equipment is decreasing rapidly and maintenance capacity is decreasing steadily. Thus, there is concern that it will become difficult to maintain infrastructure continuously.

Under these circumstances, there is demand for conversion to efficient management based on deterioration prediction of equipment. If deterioration of equipment can be predicted, it is possible to determine in advance what measures should be taken for what equipment and when, and thus to work out an efficient long-term maintenance plan.

To predict and estimate deterioration of equipment, statistical techniques are used generally. The statistical techniques, which are characterized by modelling regularity existing behind a deterioration process based on enormous amounts of inspection data on equipment, allow an average deterioration phenomenon of entire equipment to be grasped (Non-Patent Literature 1).

CITATION LIST

Non-Patent Literature

Non-Patent Literature 1: Kiyoyuki Kaito, Koichi Sugisaki, and Kiyoshi Kobayashi, "The Effects of Prior Subjective Information to Bayesian Updating Results of Deterioration Prediction," Journal of Structural Engineering published by Japan Society of Civil Engineers, Vol. 53A, pp. 775-783 (2007)

Non-Patent Literature 2: Bunzo Tsujino and Takeo Oki, "Corrosion Behavior of Steel and Application of Monitoring in Soil," Journal of the Surface Finishing Society of Japan, Vol. 40, No. 5, pp. 707-708 (1989)

Non-Patent Literature 3: Satoru Yamamoto, Kenshiro Takeko, and Satoshi Takaya, "Development of Corrosion Rate Monitoring Method (CIPE Method) of Steel in Concrete," Sabi, No. 148, pp. 2-8 (2015)

Non-Patent Literature 4: Yoshikazu Miyata and Shukuji Asakura, "Corrosion Monitoring of Metals in Soils by Electrochemical and Related Methods: Part I," Zairyo-to-Kankyo, Vol. 46, pp. 541-551 (1997)

SUMMARY OF THE INVENTION

Technical Problem

However, problems with the statistical techniques include reduced prediction accuracy caused by lack of inspection data. It is said that a few thousands to a few tens of thousands items of inspection data are needed in order to obtain statistically significant deterioration prediction results. Whereas deterioration prediction by means of the statistical techniques are effective for fictional equipment for which accumulation of inspection data is ensured by daily inspection, underground equipment, which cannot be visually checked directly, does not allow inspection data to be obtained easily, and in most cases, does not enable accumulation of inspection data that stands up to statistical analysis.

Extremely large quantities of metallic materials such as steel are used in underground equipment, including water and gas pipelines, electrical cable ducts, underground tanks, overpack materials for spent nuclear fuel, steel pipe columns, and branch line anchors. Deterioration of metallic materials buried underground progresses as a result of soil corrosion. The soil corrosion is a phenomenon in which a metal member is reduced in thickness with the metallic material rusting in an interface with the soil. Therefore, in predicting deterioration of underground metal equipment, it is effective to grasp corrosion rate of soil corrosion. Because the corrosion rate depends on environmental factors, it is necessary to find a correlation between the corrosion rate and environmental factors.

However, compared to those in the atmosphere and in water, environmental factors existing in soil are diverse, and thus a correlation between the corrosion rate and environmental factors has not been obtained yet. In such circumstances, there is a report that cites moisture percentage and air percentage in soil as important factors for soil corrosion (Non-Patent Literature 2). Although the report describes changes in corrosion rate with the moisture percentage and air percentage, the report does not clarify corrosion-rate change behavior in different soils. Because underground equipment is exposed to various soil environments, unless corrosion-rate change behavior in widely existing soils can be understood, it is difficult to achieve future prediction of deterioration.

The present invention has been made in view of the above problem and has an object to easily estimate a corrosion amount of metallic materials buried underground.

Means for Solving the Problem

The present invention provides a corrosion amount estimation apparatus that estimates a corrosion amount of a metallic material, the apparatus comprising: a soil analysis unit adapted to measure soil particle diameters of a plurality of soil samples and acquire a particle diameter distribution of soil in each of the soil samples; a corrosion measurement unit adapted to take electrochemical measurements at a plurality of soil moisture percentage values on an electrode containing the metallic material buried in each of the soil samples; a soil classification unit adapted to classify the soil in each of the soil samples into a plurality of types based on the particle diameter distribution and calculate class proportions of the plurality of types; a corrosion rate calculation unit adapted to calculate a corrosion rate regarding each of the soil samples at each of the soil moisture percentage values based on polarization resistance measured in the electrochemical measurements and identify a local maximum corrosion rate at which the corrosion rate is maximized; a corrosion estimation curve generation unit adapted to generate a corrosion estimation curve for use to estimate the corrosion amount of the metallic material using the class proportions and the local maximum corrosion rate regarding each of the soil samples; and a corrosion amount estimation unit adapted to acquire the class proportions of actual soil in which the metallic material is buried, acquire the local maximum corrosion rate corresponding to the class proportions from the corrosion estimation curve, and estimate the corrosion amount of the metallic material using the local maximum corrosion rate and a period during which the metallic material is buried in the actual soil.

The present invention provides a corrosion amount estimation method for estimating a corrosion amount of a metallic material, the method comprising: a soil analysis step of measuring soil particle diameters of a plurality of soil samples and acquiring a particle diameter distribution of soil in each of the soil samples; a corrosion measurement step of taking electrochemical measurements at a plurality of soil moisture percentage values on an electrode containing the metallic material buried in each of the soil samples; a soil classification step of classifying the soil in each of the soil samples into a plurality of types based on the particle diameter distribution and calculating class proportions of the plurality of types; a corrosion rate calculation step of calculating a corrosion rate regarding each of the soil samples at each of the soil moisture percentage values based on polarization resistance measured in the electrochemical measurements and identifying a local maximum corrosion rate at which the corrosion rate is maximized; a corrosion estimation curve generation step of generating a corrosion estimation curve for use to estimate the corrosion amount of the metallic material using the class proportions and the local maximum corrosion rate regarding each of the soil samples; and a corrosion amount estimation step of acquiring the class proportions of actual soil in which the metallic material is buried, acquiring the local maximum corrosion rate corresponding to the class proportions from the corrosion estimation curve, and estimating the corrosion amount of the metallic material using the local maximum corrosion rate and a period during which the metallic material is buried in the actual soil.

Effects of the Invention

The present invention makes it possible to easily estimate a corrosion amount of metallic materials buried underground.

DESCRIPTION OF EMBODIMENTS

A soil environment is a complicated environment in which the three phases of a solid phase, liquid phase, and gas phase coexist. The solid phase, liquid phase, and gas phase are made up of soil particles, water, and air, respectively, and when the entire soil is viewed, the proportion of the solid phase remains basically unchanged. Thus, the proportions of the liquid phase and gas phase are in a competitive relationship, and if one of the liquid phase and gas phase is monitored, changes in moisture percentage and air percentage can be understood on their own.

According to the present embodiment, a factor determining a proportion of the solid phase is defined as a soil particle diameter, corrosion rate behavior resulting from changes in soil moisture percentage describing the liquid phase is found for soil having various soil particle diameters, and a correlation between the soil particle diameter and corrosion rate is acquired. In this way, the present embodiment easily and simply estimates corrosion amounts of underground metallic materials in a wide variety of soil.

The embodiment of the present invention will be described below with reference to the drawings. In plural drawings, the same components are denoted by the same reference signs.

Figure 1:
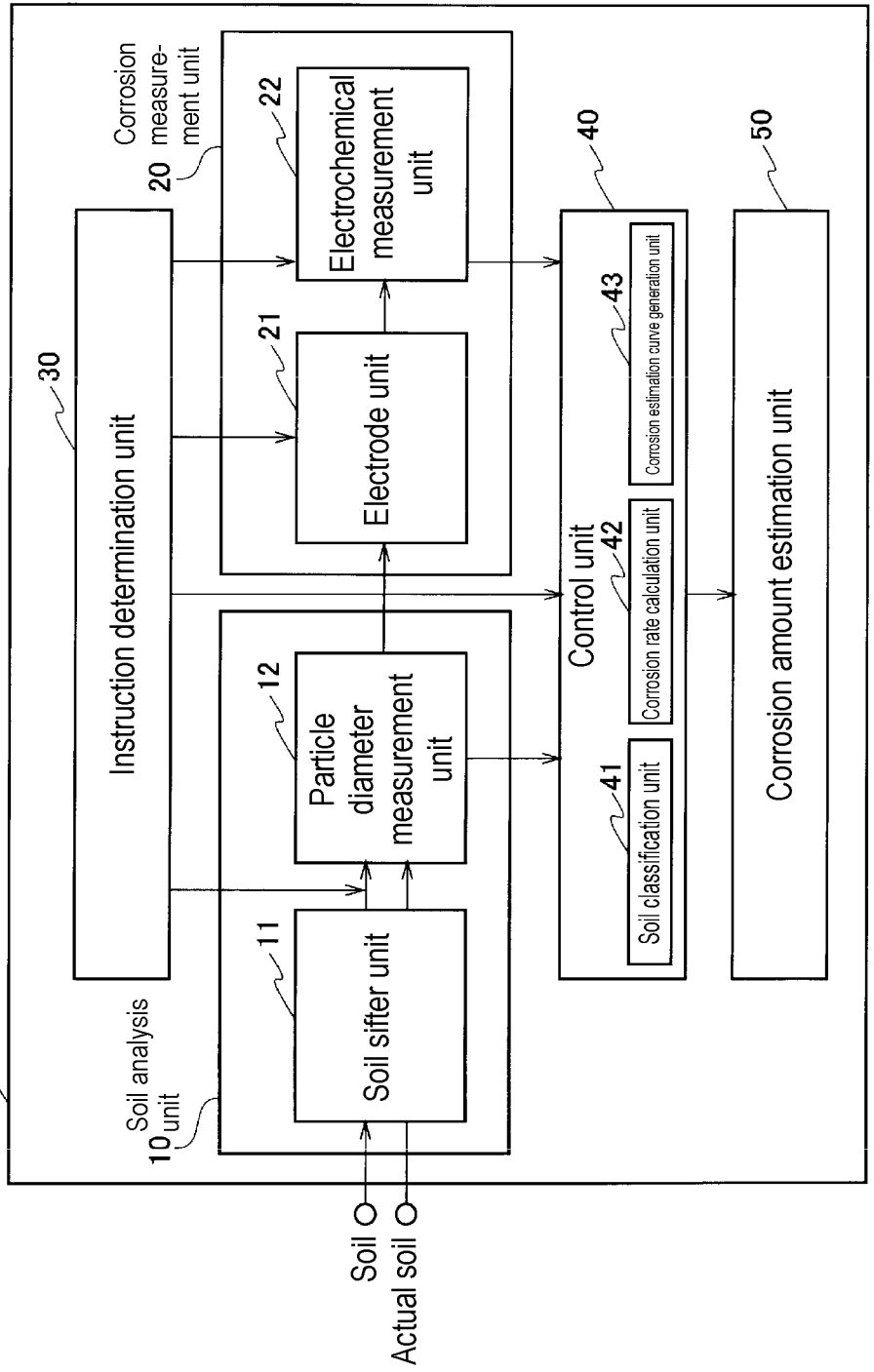
FIG. 1 is a block diagram showing a configuration of an underground metallic material corrosion amount estimation apparatus according to the present embodiment.

FIG. 1 is a functional block diagram showing a functional configuration example of an underground metallic material corrosion amount estimation apparatus according to the embodiment of the present invention, where the apparatus uses particle diameter distributions. As shown in FIG. 1, the underground metallic material corrosion amount estimation apparatus (hereinafter, the corrosion amount estimation apparatus) 1, which uses particle diameter distributions, includes a soil analysis unit 10, a corrosion measurement unit 20, an instruction determination unit 30, a control unit 40, and a corrosion estimation unit 50.

The soil analysis unit 10 makes plural soil samples, measures particle diameters of soil in the plural soil samples, and acquires a particle diameter distribution (e.g., particle size distribution curve) of each of the soil samples. The illustrated soil analysis unit 10 includes at least one soil sifter unit 11 and at least one particle diameter measurement unit 12.

The soil sifter unit 11 is made up, for example, of plural soil sifters stacked one on top of another, and it is assumed that meshes of the soil sifters become finer from top to bottom. The soil sifter unit 11 divides soil introduced from outside into different parts according to soil particle diameter using at least one sifter and makes soil samples by mixing the soil remaining on the sifters in any desired proportions on instructions from the instruction determination unit 30. Note that the soil sifter unit 11 makes plural soil samples on instructions from the instruction determination unit 30.

The particle diameter measurement unit 12 measures the particle diameters of the soil samples made by the soil sifter unit 11 and thereby acquires particle diameter distributions of the soil samples. According to the present embodiment, a particle size distribution curve described later is used as the particle diameter distribution, but this is not restrictive.

The corrosion measurement unit 20 takes electrochemical measurements at plural soil moisture percentages on an electrode containing a metallic material-to-be-estimated buried in each of the soil samples made by the soil analysis unit 10. The illustrated corrosion measurement unit 20 includes at least one electrode unit 21 and at least one electrochemical measurement unit 22.

The electrode unit 21 includes electrodes used to carry out electrochemical measurements, a soil moisture sensor used to measure soil moisture percentages, and a water supply device used to add water to the soil sample. The electrodes and soil moisture sensor of the electrode unit 21 are buried in each soil sample after measurements in the particle diameter measurement unit 12. The electrodes of the electrode unit 21 include a working electrode buried in sample soil by being made of the same material as the underground metallic material whose corrosion amount is to be estimated.

The electrochemical measurement unit 22 adds water sufficient in amount to saturate the soil in the soil sample to the soil sample in which the electrode unit 21 is buried, takes electrochemical measurements by reducing the soil moisture percentage from a saturated state, and measures corrosion resistance (polarization resistance) at plural soil moisture percentages to calculate the corrosion rate.

Using a particle size distribution acquired by the soil analysis unit 10 and measurement results (polarization resistance) obtained as a result of measurements by the corrosion measurement unit 20, the control unit 40 generates a corrosion estimation curve for use to estimate a corrosion amount. The illustrated control unit 40 includes a soil classification unit 41, a corrosion rate calculation unit 42, and a corrosion estimation curve generation unit 43.

The soil classification unit 41 classifies the soil in each of the soil samples plural types based on the particle diameter distribution (particle size distribution curve) acquired by the particle diameter measurement unit 12 and calculates class proportions of the plural types. Specifically, the soil classification unit 41 calculates the class proportions, which indicate in what proportions particles are contained in predetermined particle diameter ranges, and records calculation results in a storage unit such as memory.

The corrosion rate calculation unit 42 calculates a corrosion rate regarding each of the soil samples at each of the soil moisture percentages based on polarization resistance measured in the electrochemical measurements and identifies a local maximum corrosion rate at which the corrosion rate is maximized. Specifically, the corrosion rate calculation unit 42 calculates the corrosion rate at each of the soil moisture percentages based on the polarization resistance produced as a result of measurements taken by the electrochemical measurement unit 22, and generates a corrosion rate curve by plotting the corrosion rates at the respective soil moisture percentages. Then, using the corrosion rate curve, the corrosion rate calculation unit 42 identifies a local maximum corrosion rate at which the corrosion rate is maximized.

Using the class proportions and the local maximum corrosion rate regarding each of the soil samples, the corrosion estimation curve generation unit 43 generates a corrosion estimation curve, which represents a relationship between the class proportion and local maximum corrosion rate, in order to estimate the corrosion amount of the underground metallic material. Specifically, the corrosion estimation curve generation unit 43 generates a corrosion estimation curve by plotting local maximum values (local maximum corrosion rates) on corrosion rate curves against the respective class proportions obtained from the particle size distribution curves of plural soil samples.

A corrosion amount estimation unit 50 acquires the class proportion of actual soil in which the metallic material-to-be-estimated is buried, acquires the local maximum corrosion rate corresponding to the class proportion from the corrosion estimation curve generated by the corrosion estimation curve generation unit 43, and estimate the corrosion amount of the metallic material using the local maximum corrosion rate and a period during which the metallic material is buried in the actual soil.

Next, a process of the corrosion amount estimation apparatus 1 according to the present embodiment will be described.

Figure 2:
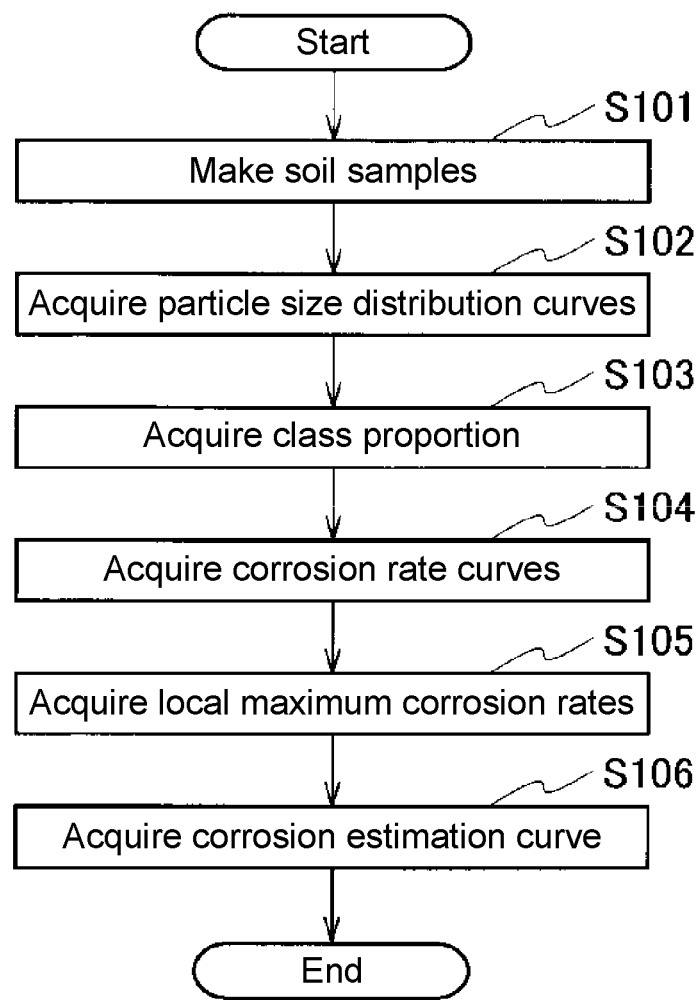
FIG. 2 is a flowchart showing a flow of a process of generating a corrosion estimation curve.

FIG. 2 is a flowchart showing a flow of a corrosion estimation curve generation process of the corrosion amount estimation apparatus 1. The corrosion amount estimation apparatus 1 generates the corrosion estimation curve using plural sample soils.

Note that because one maximum corrosion rate per soil sample is plotted on the corrosion estimation curve described later, the corrosion amount estimation apparatus 1 makes a sufficient number (at least three) of soil samples to derive a corrosion estimation curve. By increasing the number of soil samples, it is possible to generate a more accurate corrosion estimation curve. Note that steps S101 to S105 are carried out for each soil sample.

The soil sifter unit 11 makes plural sample soils (step S101). Specifically, the soil sifter unit 11 classifies the soil introduced from outside into different parts according to soil particle diameter using at least one sifter. For example, when four soil sifters are stacked one on top of another and the roughness of soil sifter meshes is 1 mm, 500 µm, 50 µm, and 500 nm starting from the top, particles larger than 1 mm are left on the 1-mm sifter, particles from 500 µm to 1 mm are left on the 500-µm sifter, particles from 50 µm to 500 µm are left on the 50-µm sifter, particles from 500 nm to 50 µm are left on the 500-nm sifter, and particles smaller than 500 nm pass through all the sifters.

However, for reasons that the soil sifter meshes can get clogged with soil, that sifting time can be insufficient, and the like, the particle diameters of soil particles remaining on the sifters are only rough measures, and strict particle diameter measurement in step S102 that follows is needed.

Using plural soils (the soils remaining on the respective sifters and soils passing through all the sifters) resulting from classification by the sifters, the soil sifter unit 11 makes plural sample soils. The instruction determination unit 30 instructs the soil sifter unit 11 in what proportion each of the sample soils should contain the plural soils resulting from the classification by the sifters. In response to the instructions from the instruction determination unit 30, the soil sifter unit 11 extracts the specified plural soils in the specified proportions from the plural soils resulting from the classification by the sifters and makes a soil sample by mixing all the extracted soils.

The particle diameter measurement unit 12 measures the particle diameters of the produced soil sample and thereby acquires a particle diameter distribution of the soil (step S102). Here, it is assumed that a particle size distribution curve is generated as the particle diameter distribution. As a concrete technique for particle diameter measurements, for example, a soil particle size test method described in JIS A 1204:2009 may be adopted or a laser diffraction/scattering particle size analysis method may be adopted.

However, the soil particle size test method described in JIS has to apply sifting analysis to particles equal to or larger than 75 μm while applying sedimentation analysis to particles smaller than 75 μm and requires a soil sample 500 mL or above in volume for analysis in addition to taking a long time until results are obtained. In contrast, the laser diffraction/scattering particle size analysis requires a soil sample only a few mL in volume for analysis while taking a very short time on the order of a few tens of seconds for measurements. Thus, preferably the laser diffraction/scattering particle size analysis is applied to particle diameter measurements in step S102.

Note that the laser diffraction/scattering particle size analysis may not provide proper results depending on the soil sampling method if a particle diameter distribution range of the soil sample is wide and the soil sample is mixed insufficiently. Therefore, preferably plural soil samples are acquired by mixing each soil sample sufficiently and the average of the soil samples is used as a final measurement result.

Figure 3:
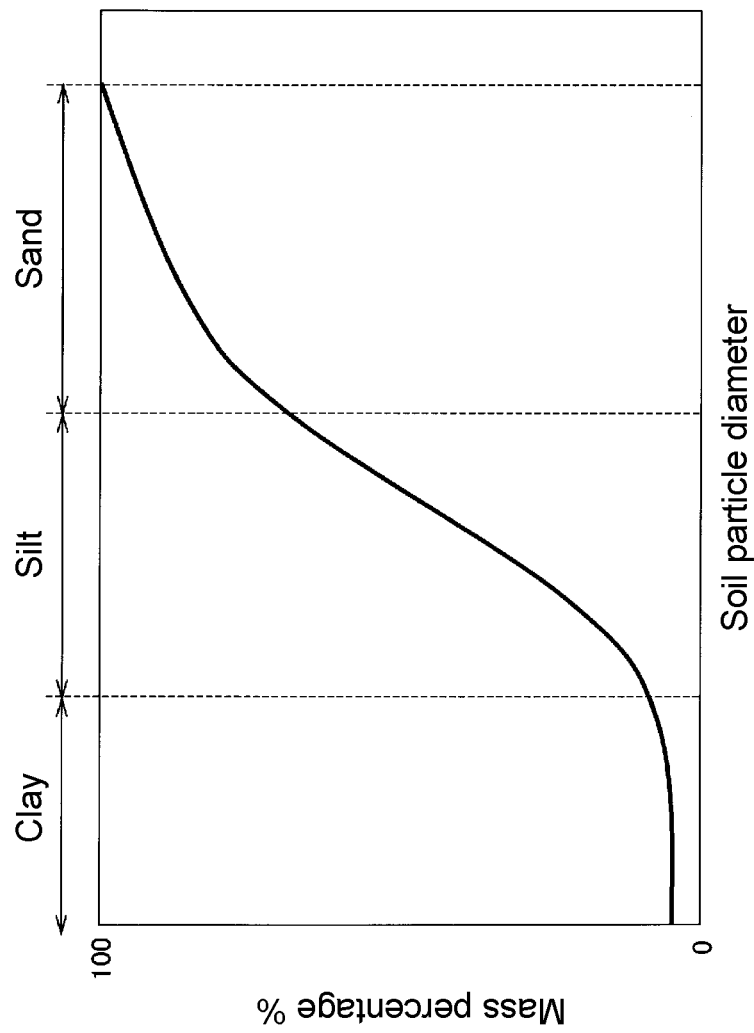
FIG. 3 is a diagram showing an example of a particle size distribution curve obtained by a particle diameter measurement unit.

FIG. 3 shows an example of a particle size distribution curve of one soil sample generated by the particle diameter measurement unit 12. For each soil sample, the particle diameter measurement unit 12 generates a particle size distribution curve that represents mass proportions corresponding to particle diameters measured in the soil sample. Then, the particle diameter measurement unit 12 sends out the particle size distribution curve generated for each soil sample to the control unit 40.

The control unit 40 calculates in what proportions particles are contained (hereinafter, class proportions) in predetermined particle diameter ranges, and records the calculation results in a storage unit such as memory (step S103).

Regarding class proportions, the particle diameter range of each class and the number of classes can be set as desired. For example, classes standardized by an engineering classification method of ground materials according Japanese Geotechnical Society Standard JGS 0051 may be used. Because most of actual soil is made up of soil particles 2 mm or below in diameter, according to the present embodiment, based on the engineering classification method of ground materials, particles from 75 μm to 2 mm are classified as "sand," particles from 5 μm to 75 μm are classified as "silt," and particles smaller than 5 μm are classified as "clay."

Then, regarding each soil sample, the control unit 40 calculates proportions of the three classes using the particle size distribution curve generated by the particle diameter measurement unit 12. In this case, "classes" indicate "sand," "silt," and "clay" distinguished from one another by the particle diameter. The control unit 40 calculates the class proportions from mass percentage represented by the ordinate of the particle size distribution curve shown in FIG. 3. If the classification method of JGS 0051 is adopted, the class proportions of a certain soil sample is calculated, for example, as 40% sand, 50% silt, and 10% clay. The control unit 40 stores the calculated class proportions of each soil sample in the storage unit.

Note that preferably the particle diameter ranges of the respective classes are set such that the sum total of all the class proportions will be 100% or infinitely close to 100%.

Next, generation of the corrosion rate curve done for each soil sample will be described (step S104).

The electrode of the electrode unit 21 varies in configuration depending on the electrochemical measurement technique used by the electrochemical measurement unit 22. For example, when a two-electrode method is used, an electrode configuration includes two electrodes: a working electrode and a counter electrode. Note that the working electrode and counter electrode are made of the same material as the underground metallic material whose corrosion amount is to be estimated.

When a three-electrode method is used, an electrode configuration includes three electrodes: a working electrode, a counter electrode, and a reference electrode. Note that the working electrode is made of the same material as the underground metallic material whose corrosion amount is to be estimated, that the counter electrode is made, for example, of platinum, carbon, or the like used commonly, and that the reference electrode may be, for example, a silver-silver chloride electrode, calomel electrode, or the like used commonly.

The water supply device of the electrode unit 21 is used to add water to the soil sample in which electrodes are buried. Although the type of water supply is not called into question, preferably the soil sample is not disturbed much by water pressure.

The electrochemical measurement unit 22 carries out electrochemical measurements to calculate the corrosion rate of each soil sample. Electrochemical calculation of corrosion rates generally uses a technique that involves measuring reaction resistance (polarization resistance Rp) along with the progress of corrosion (Non-Patent Literature 2). As the electrochemical technique, for example, a DC polarization resistance method or an AC impedance method is used.

The measurement using the DC polarization resistance method involves sweeping DC potential within a potential range that allows a resistance value to be calculated from obtained current-potential characteristics with reference to self-potential without roughening metal surfaces. For example, the measurement may be carried out in a potential range of ±5 [mV], which corresponds to applied potential in the AC impedance method considered to have a reduced impact on metal surfaces in electrochemical measurements. The polarization resistance Rp is calculated from a slope of the obtained current-potential characteristics. As a method for calculating the slope, for example, a least-squares method or an extrapolation method may be used.

The measurement using the AC impedance method is carried out from a high frequency toward a low frequency, and a circular arc appears in each of a high frequency region and low frequency region.

Figure 4:
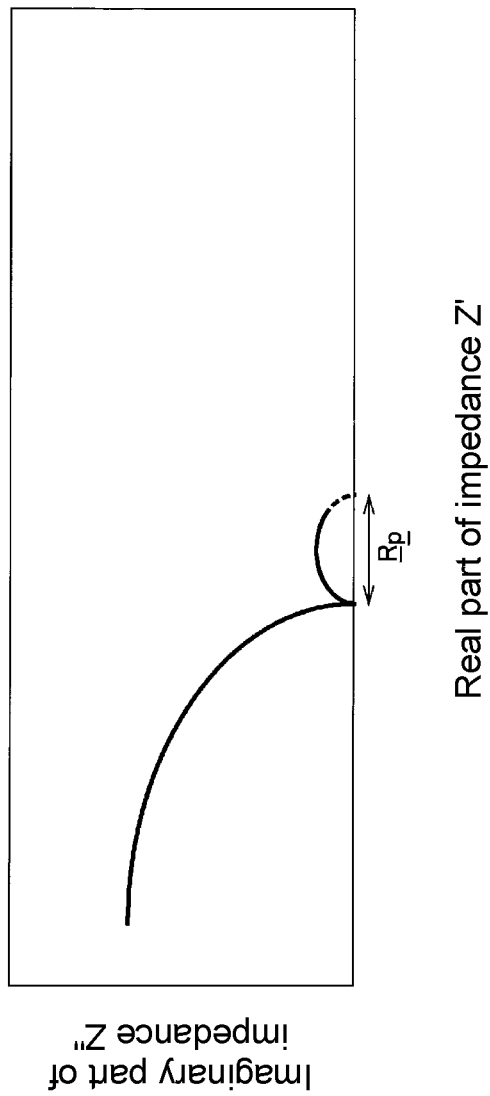
FIG. 4 is a diagram showing an example of measurement results (Nyquist diagram) of electrochemical measurement.

FIG. 4 shows an example of a Nyquist diagram obtained by the AC impedance method. The polarization resistance Rp, which is considered to originate in the circular arc in the low frequency region, is calculated from abscissa values from the start point to the end point of the circular arc in the low frequency region (the abscissa represents the real part of impedance Z' [Ω·cm$^2$]). Preferably an applied AC potential is ±5 [mV] considered to have a reduced impact on metal surfaces.

Note that because the polarization resistance Rp obtained by the DC polarization resistance method is the resistance value of the entire measurement system, it is conceivable that in the measurement of the soil sample, the value of soil resistance may appear too great to be ignored relative to the polarization resistance Rp. On the other hand, the AC impedance method can separate the resistance value measured by the frequency of applied potential. For example, in FIG. 4, the circular arc in the high frequency region reflects resistance originating in soil while the circular arc in the low frequency region reflects only the polarization resistance Rp. Therefore, the AC impedance method can find only the polarization resistance Rp accurately. Thus, preferably the electrochemical measurement unit 22 takes electrochemical measurements on sample soil using the AC impedance method.

Figure 5:
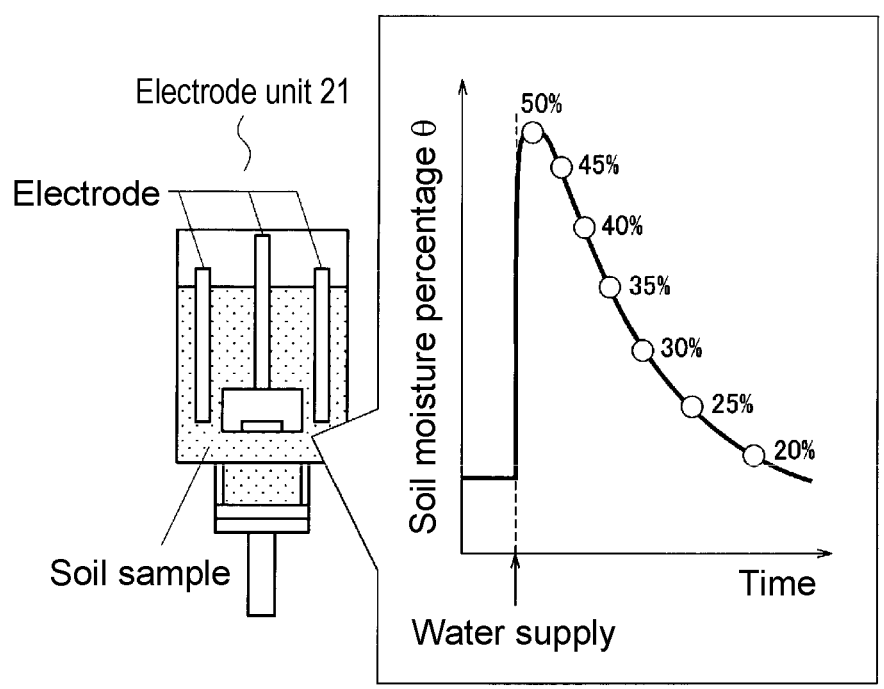
FIG. 5 is a diagram showing an example of timing to take electrochemical measurements.

FIG. 5 is a diagram showing an example of timing for the electrochemical measurement unit 22 to take electrochemical measurements of a soil sample. The illustrated electrode unit 21 has three electrodes buried in the sample soil.

After supplying water sufficient in amount to saturate the soil sample in the electrode unit 21, the electrochemical measurement unit 22 carries out electrochemical measurements at plural soil moisture percentages θ specified by the instruction determination unit 30, by gradually reducing the soil moisture percentage θ. The water supply device (not shown) of the electrode unit 21 supplies water to the sample soil until the soil sample saturates.

In the illustrated example, the soil sample saturates at a soil moisture percentage θ of 50% and the electrode unit 21 gradually reduces the soil moisture percentage θ of the soil sample. The electrochemical measurement unit 22 carries out electrochemical measurements, for example, at intervals of 5%: at 50%, 45%, 40%, and so on. As a lower limit of the soil moisture percentage θ used for the measurements, preferably the lowest value (20% in the illustrated example) observed in actual soil is adopted.

The electrochemical measurement unit 22 may carry out electrochemical measurements at predetermined plural soil moisture percentages θ on instructions from the instruction determination unit 30. In that case, the instruction determination unit 30 constantly monitors (acquires) the soil moisture percentage θ (sensor value) detected by the soil moisture sensor of the electrode unit 21 and transmits measurement instructions to the electrochemical measurement unit 22 each time the soil sample reaches a predetermined soil moisture percentage θ (e.g., 50%, 45%, 40%, or the like). Each time measurement instructions are received, the electrochemical measurement unit 22 carries out an electrochemical measurement.

Alternatively, the electrochemical measurement unit 22 may carry out electrochemical measurements at predetermined plural soil moisture percentages θ autonomously. In that case, the electrochemical measurement unit 22 holds plural soil moisture percentages θ of a measuring object by acquiring them from the instruction determination unit 30 in advance. Then, the electrochemical measurement unit 22 constantly monitors the soil moisture percentage θ detected by the soil moisture sensor of the electrode unit 21 and carries out electrochemical measurements when the soil sample reaches a predetermined soil moisture percentage θ.

Note that measurement timing for the electrochemical measurement unit 22 can be changed as desired on instructions from the instruction determination unit 30. Note that measurements are carried out by the electrochemical measurement unit 22 until the instruction determination unit 30 or electrochemical measurement unit 22 detects that the soil moisture percentage θ has reached a predetermined lower limit.

Figure 6:
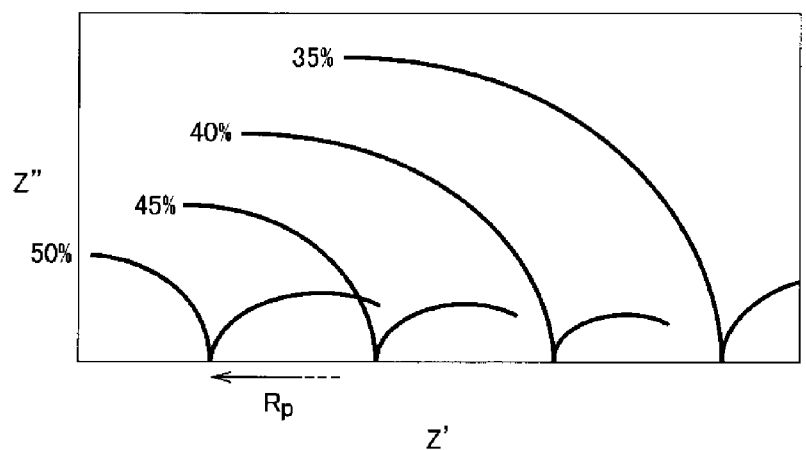
FIG. 6 is a diagram showing an example of measurement results (Nyquist diagram) of electrochemical measurements at plural soil moisture percentages.

FIG. 6 shows an example of a Nyquist diagram obtained by electrochemical measurements of the AC impedance method at plural soil moisture percentages θ. A Nyquist diagram is acquired at each of the soil moisture percentages θ used for the measurements, and consequently the polarization resistance Rp based on the circular arc in the low frequency region can be acquired.

As a method for reducing the soil moisture percentage θ, for example, a filter a few tens of microns in diameter may be laid on a bottom face of the electrode unit 21 to let water to drain spontaneously. Also, when soil conditions are such that water is very slow to drain spontaneously, the electrode unit 21 may be equipped with a dryer to reduce the soil moisture percentage θ.

Depending on the value of the soil moisture percentage θ, it is conceivable that the soil moisture percentage θ may change (decrease) greatly during a period from start to end of the electrochemical measurement. Thus, preferably the corrosion measurement unit 20 is equipped with a mechanism for preventing the soil moisture percentage θ from varying during the electrochemical measurement. For example, relative humidity of the electrode unit 21 may be set to an infinitely high value during measurement to prevent evaporation of moisture or a sealing valve may be attached to the bottom face of the electrode unit 21 to prevent drainage.

The electrochemical measurement unit 22 sends out measurement results including the polarization resistance Rp measured at each soil moisture percentage θ to the control unit 40. The control unit 40 calculates corrosion current density icorr from the polarization resistance Rp at each soil moisture percentage θ using the following formula.

Formula 1

$$i_{corr} = K \cdot \frac{1}{R_p} \quad (1)$$

where icorr is corrosion current density [A/cm$^2$], K is a conversion factor [V], and Rp is polarization resistance [Ω·cm$^2$]. The conversion factor K is calculated in advance. That is, the conversion factor K is calculated using the following formula by deriving the Tafel slope from anodic and cathodic polarization curves (Non-Patent Literature 3).

Formula 2

$$K = \frac{\beta_a - \beta_c}{2.3(\beta_a + \beta_c)} \quad (2)$$

where βa is an anodic curve [V/decade] and βc is a cathodic curve [V/decade]. Alternatively, the conversion factor K may be calculated by assuming that βa=βc=0.1 [V/decade] without measuring the Tafel slope (Non-Patent Literature 4).

Next, the control unit 40 calculates a corrosion rate r using the following formula.

Formula 3

$$r = \frac{M}{z\rho F} \cdot i_{corr} \quad (3)$$

where r is a corrosion rate [cm/sec], z is ion valence, ρ is density [g/cm$^2$], F is the Faraday constant [C], and M is an atomic weight [g/mol]. Values of z (ion valence), ρ (density), and M (atomic weight) are fixed for each material used for the working electrode of the electrode unit 21. For example, if iron (Fe) is used for the working electrode, then Z=2, ρ=7.8, and M=55.8. By multiplying the calculated corrosion rate r [cm/sec] by 3.15×10$^8$, the unit is converted into [mm/year].

Then, by plotting the soil moisture percentage θ on the abscissa, and the corrosion rate r on the ordinate, the control unit 40 acquires a corrosion rate curve for each of soil samples differing in soil particle diameter from one another (step S104).

Figure 7:
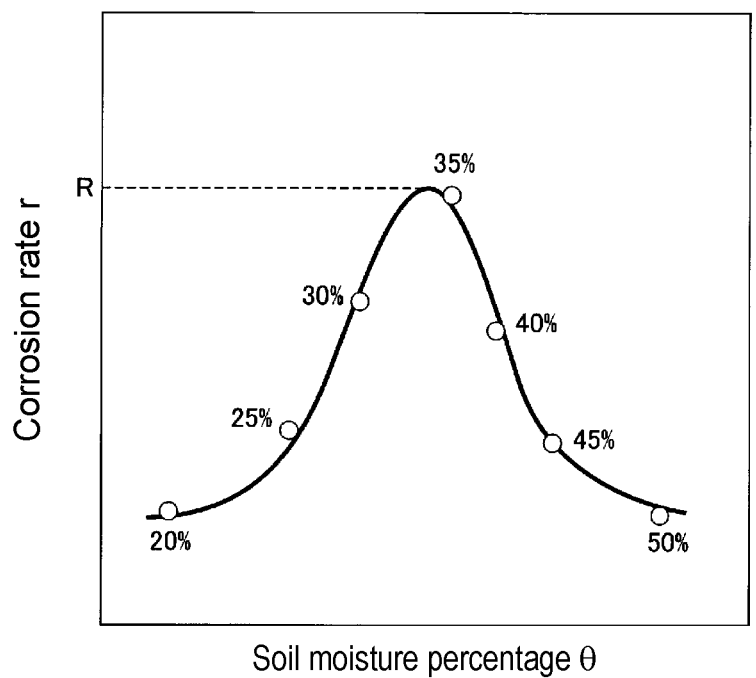
FIG. 7 is a diagram showing an example of a corrosion rate curve of one soil sample.

FIG. 7 shows an example of a corrosion rate curve of one soil sample. The corrosion rate curve shows a local maximum value R of the corrosion rate at a specific soil moisture percentage θ. The reason why the corrosion rate reaches a local maximum value R at a specific soil moisture percentage θ is that diffusion of oxygen and wetted area of metal surfaces, which are considered to be governing factors of soil corrosion, affect each other relatively. Reaction formula (4) and Formula (5) describing progress of soil corrosion are shown below.

$$Fe \rightarrow Fe^{2+} + 2e^{-} \quad (4)$$

$$O_2 + 2H_2O + 4e^{-} \rightarrow 4OH^{-} \quad (5)$$

Because soil corrosion is an oxidation-reduction reaction, the reaction proceeds when Formula (4) and Formula (5) proceed simultaneously. It can be seen from Formula (5) that a corrosion reaction requires water and oxygen. That is, in a soil environment in which a liquid phase and gas phase are in a competitive relationship, oxygen is small in amount under conditions in which soil moisture percentage is high, but even if oxygen is contained abundantly, the soil moisture percentage becomes low. Thus, under specific soil moisture percentage conditions in which water and oxygen exist in a balanced manner, the corrosion rate exhibits a local maximum value R. Also, the specific soil moisture percentage, which depends on the proportions that the liquid phase and gas phase can make up, shows a correlation with the soil particle diameter that determines the proportion of the solid phase.

Next, for each soil sample, the control unit 40 calculates a local maximum value of the corrosion rate, i.e., a local maximum corrosion rate R, using the corrosion rate curve and records the calculated local maximum corrosion rate R in a recording unit such as memory (step S105).

The control unit 40 finds the local maximum corrosion rate R, for example, from a fitting curve for a corrosion rate curve. As shown in FIG. 7, since the corrosion rate curve is an upward convex curve, curve fitting by the use of, for example, a Lorentzian function can be applied to the corrosion rate curve. An example of a mathematical expression of a Lorentzian function is shown below.

Formula 4

$$f(x) = \frac{h}{1 + \left(\frac{x-u}{w}\right)^2} + b \quad (6)$$

where h is a peak height, u is a soil moisture percentage θ at which a peak appears, w is a half-width, and b is a background. That is, the local maximum corrosion rate R can be calculated using the following formula.

Formula 5

$$R = h + b \quad (7)$$

Figure 8:
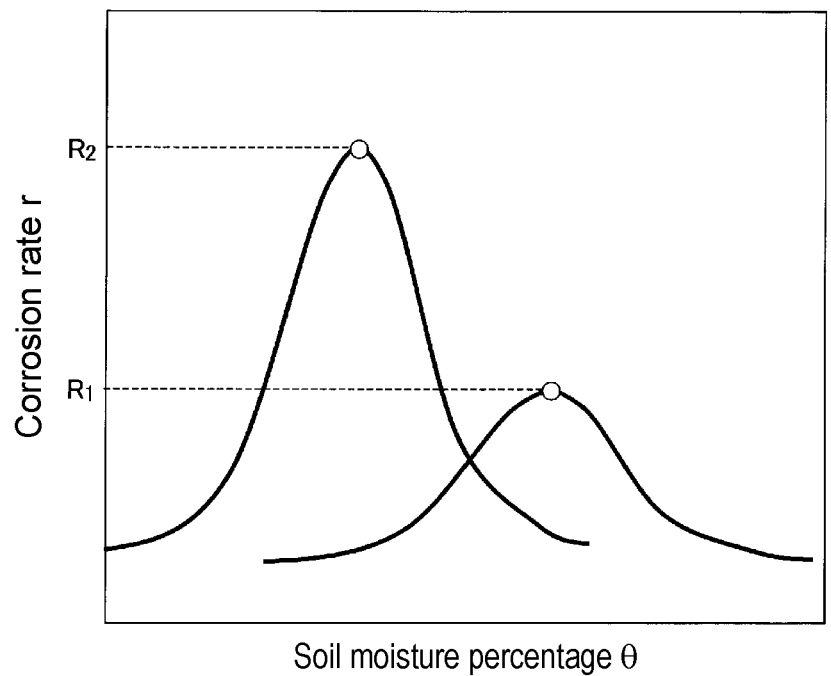
FIG. 8 is a diagram showing an example of corrosion rate curves of two soil samples.

FIG. 8 shows corrosion rate curves of two soil samples and local maximum corrosion rates R1 and R2 of the respective corrosion rate curves.

Next, using class proportions calculated from particle size distribution curves acquired from respective soil samples having various soil particle diameters, as well as using local maximum corrosion rates R calculated from corrosion rate curves, the control unit 40 generates a corrosion estimation curve for use to estimate a corrosion amount of a metallic material buried in actual soil having various soil particle diameters (step S106). The corrosion estimation curve represents a relationship between the class proportions of soil and the local maximum corrosion rates R.

Figure 9:
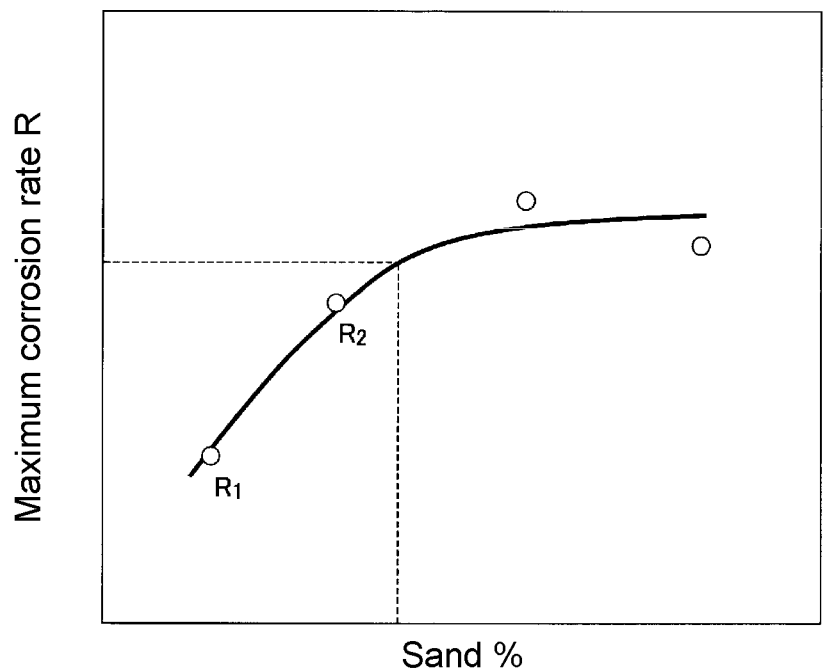
FIG. 9 is a diagram showing an example of a corrosion estimation curve in which local maximum corrosion rates on corrosion rate curves are plotted against the proportion (class proportion) of sand obtained from a particle size distribution curve.

FIG. 9 is a diagram showing an example of a corrosion estimation curve generated by varying the class proportion of sand. The corrosion estimation curve is a graph generated from soil samples by plotting the class proportion (class proportion of sand in the illustrated example) on the abscissa and the local maximum corrosion rate R on the ordinate. The corrosion estimation curve of FIG. 9 is generated by plotting four soil samples. Note that to draw a corrosion estimation curve, it is necessary to plot at least three local maximum corrosion rates R, and thus the number of soil samples needed to be made is three or more. Note that the accuracy of the generated corrosion estimation curve increases in proportion to the number of calculated local maximum corrosion rates R.

Since the corrosion rate has a correlation with the soil particle diameter as described above, the corrosion rate has a correlation with any class proportion selected arbitrarily.

For example, when two classes—class A and class B—are set, if the proportion of either A or B is known, the proportion of the other class is determined on its own. That is, either of A and B may be selected as the abscissa of the corrosion estimation curve and it is sufficient to acquire a corrosion estimation curve of class A vs. local maximum corrosion rate R or class B vs. local maximum corrosion rate R. That is, when there are two classes, the required number of corrosion estimation curves to be acquired is one two-dimensional corrosion estimation curve (see FIG. 9).

Also, when three classes, i.e., sand, silt, and clay, according to the engineering classification method of ground materials are set, a corrosion estimation curve may be generated by fixing one class proportion, selecting one of the two remaining classes, and plotting the local maximum corrosion rate R against the selected class proportion. For example, by fixing the class proportion of clay to 0%, one of corrosion estimation curve—silt vs. local maximum corrosion rate R or sand vs. local maximum corrosion rate R—is generated first. Next, by fixing clay to 10%, a corrosion estimation curve is generated in the same manner as described above. This is repeated until the class proportion of clay reaches 100% to acquire corrosion estimation curves repeatedly. In this case, eleven corrosion estimation curves are acquired.

When corrosion estimation curves of silt vs. local maximum corrosion rate R are acquired repeatedly with clay fixed, the control unit 40 generates a three-dimensional corrosion estimation curve using the acquired plural corrosion estimation curves with clay, silt, and local maximum corrosion rate R taken on axes. Also, when corrosion estimation curves of sand vs. local maximum corrosion rate R are acquired repeatedly with clay fixed, a three-dimensional corrosion estimation curve is generated with clay, sand, and local maximum corrosion rate R taken on axes.

Note that although in the example described above, a three-dimensional corrosion estimation curve is generated from eleven two-dimensional corrosion estimation curves, this is not restrictive. To draw a three-dimensional corrosion curve, at least three two-dimensional corrosion estimation curves are needed, and thus the required number of two-dimensional corrosion estimation curves is three or more. Note that the accuracy of the generated three-dimensional corrosion curve increases in proportion to the number of two-dimensional corrosion estimation curves.

Through the process of FIG. 2, using plural sample soils, the corrosion amount estimation apparatus 1 generates a corrosion estimation curve used to estimate the corrosion amount of a metallic material buried in actual soil having various soil particle diameters.

Next, a processing method for estimating the corrosion amount of an underground metallic material will be described.

Figure 10:
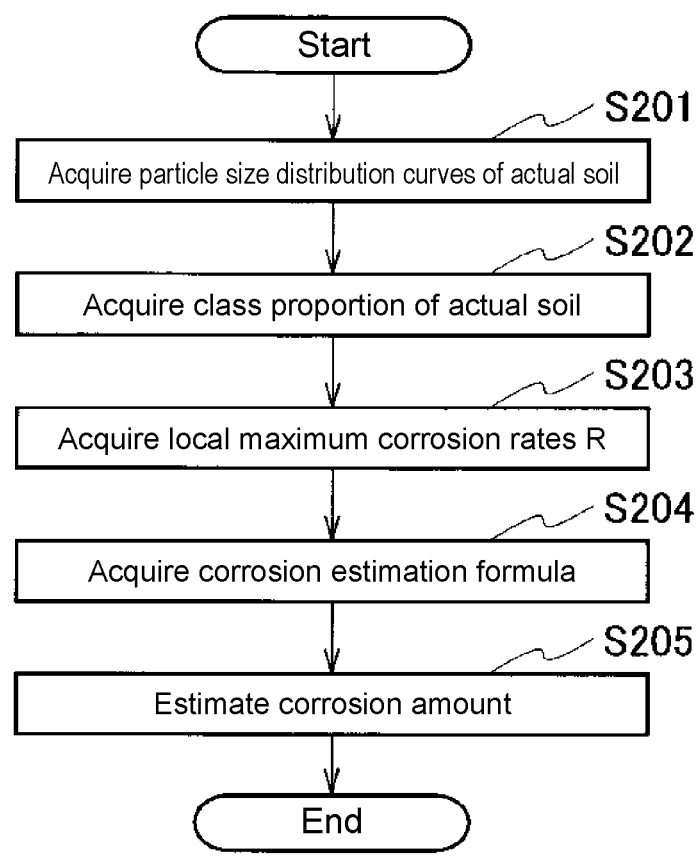
FIG. 10 is a flowchart showing a flow of a corrosion amount estimation process.

FIG. 10 is a flowchart showing a flow of a corrosion amount estimation process performed by the corrosion amount estimation apparatus 1. The corrosion amount estimation apparatus 1 estimates the corrosion amount using soil (hereinafter, "actual soil") existing in the neighborhood of an underground metallic material whose corrosion amount is to be estimated.

First, the corrosion amount estimation apparatus 1 samples actual soil in the neighborhood of an underground metallic material-to-be-estimated and introduces the actual soil into the soil analysis unit 10. In so doing, the sampled actual soil is introduced into the particle diameter measurement unit 12 by bypassing the soil sifter unit 11. As with step S102 of FIG. 2, the particle diameter measurement unit 12 measures the particle diameter of the actual soil and generates particle size distribution curves (step S201). The particle diameter measurement unit 12 sends out the generated particle size distribution curves to the control unit 40.

As with step S103 of FIG. 2, the control unit 40 calculates the class proportions of the actual soil (step S202). Here, the same classes as in step S103 of FIG. 2 are used. Note that when the particle diameter distribution of the actual soil is known, the collection of the actual soil and steps S201 and S202 may be omitted.

Using the class proportions of the actual soil and the corrosion estimation curve generated in FIG. 2, the corrosion estimation unit 50 acquires local maximum corrosion rates R (step S203). Specifically, when there are two classes, two-dimensional corrosion estimation curve such as shown in FIG. 9 is generated. By applying curve fitting to the corrosion estimation curve of FIG. 9, the corrosion estimation unit 50 derives a relational expression between "maximum corrosion rate R" and "proportion of sand (sand %)" and substitutes the proportion of sand in the actual soil into the relational expression, thereby calculating the maximum corrosion rate R.

When there are three classes, a three-dimensional corrosion estimation curve of A, B, (or C), and local maximum corrosion rates R is generated. By applying curve fitting to the corrosion estimation curve, the corrosion estimation unit 50 derives a relational expression of "maximum corrosion rate R" with "proportion of A" and "proportion of B" and substitutes the proportion of A and proportion of B in the actual soil into the relational expression, thereby calculating the maximum corrosion rate R.

The corrosion estimation unit 50 acquires a corrosion estimation formula that uses the calculated local maximum corrosion rates R of the actual soil (step S204). As a method for calculating a corrosion amount using local maximum corrosion rates R, power law formula (8) known as an empirical model for predicting corrosion progress may be used as a corrosion estimation formula.

Formula 6

$$D = RT^n \qquad (8)$$

where D is a corrosion amount [mm/year], T is an elapsed time period [year] of an underground metallic material, and n is a corrosivity evaluation value of the material. However, regarding the value of n, which is empirically said to be 0.4 to 0.6, the intermediate value of 0.5 may be adopted. Note that T (elapsed time period) is the period for which the underground metallic material has been buried in the actual soil.

Figure 11:
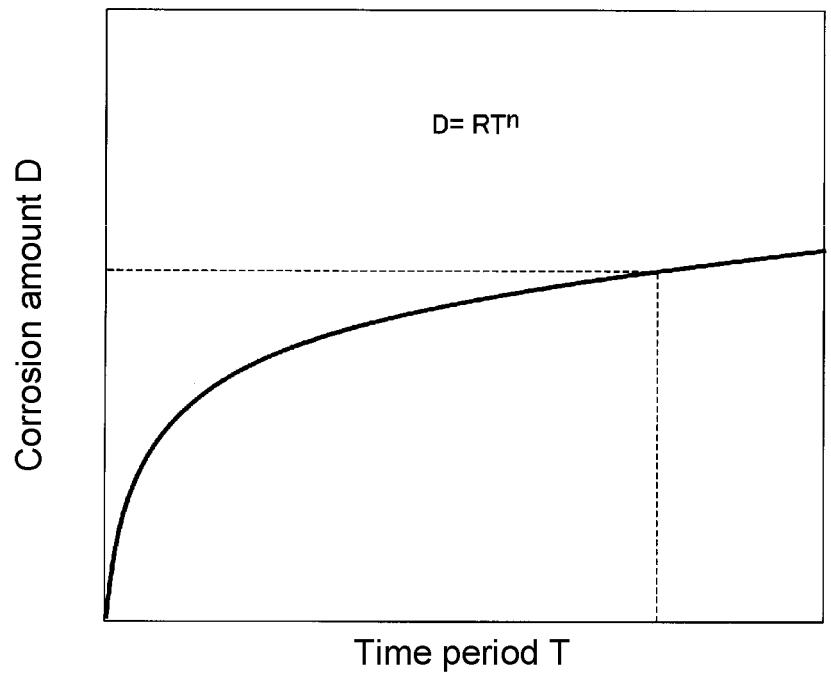
FIG. 11 is a diagram showing an example of a corrosion amount estimation formula.

FIG. 11 shows an example of a graph in which the ordinate represents the corrosion amount D of the corrosion estimation formula in Formula (8) and the abscissa represents the elapsed time period T.

The corrosion estimation unit 50 substitutes the elapsed time period T entered or held as a parameter of corrosion estimation into the corrosion estimation formula and thereby estimates the corrosion amount of the underground metallic material (step S205). A user of the corrosion amount estimation apparatus 1 enters how many years have elapsed since the underground metallic material-to-be-estimated was buried to the corrosion estimation unit 50. Alternatively, the corrosion amount estimation apparatus 1 may hold the elapsed time period T of the underground metallic material-to-be-estimated in a storage unit such as memory.

According to the present embodiment described above, by using a corrosion estimation curve generated from particle diameter distributions and local maximum corrosion rates of plural soil samples, it is possible to easily and simply estimate the corrosion of an underground metallic material without actually measuring the corrosion amount of the underground metallic material. That is, according to the present embodiment by using the soil particle diameter, which is a determinant factor of moisture percentage and air percentage in soil, it is possible to easily estimate the corrosion amount of an underground metallic material without actually measuring the corrosion amount of the underground metallic material.

For example, a general-purpose computer system equipped with a CPU (Central Processing Unit, processor), memory, storage (HDD: Hard Disk Drive; SSD: Solid State Drive), a communications device, input device, and output device can be used as the control unit 40 and corrosion estimation unit 50 of the corrosion amount estimation apparatus 1 described above. On the computer system, as the CPU executes programs for the control unit 40 and corrosion estimation unit 50 when the programs are loaded into memory, functions of the control unit 40 and corrosion estimation unit 50 are implemented. Also, the programs for the control unit 40 and corrosion estimation unit 50 may be stored in a computer-readable recording medium such as a HDD, SSD, USB memory, CD-ROM, DVD-ROM, or MO or distributed via a network.

Note that the present invention is not limited to the embodiment described above and that various changes can be made without departing from the scope of the present invention.

REFERENCE SIGNS LIST

1 Corrosion amount estimation apparatus
10 Soil analysis unit
11 Soil sifter unit
12 Particle diameter measurement unit
20 Corrosion measurement unit
21 Electrode unit
22 Electrochemical measurement unit
30 Instruction determination unit
40 Control unit
50 Corrosion estimation unit

The invention claimed is:

1. A corrosion amount estimation method for estimating a corrosion amount of a metallic material, the method comprising:
   a soil analysis step of measuring soil particle diameters of a plurality of soil samples and acquiring a particle diameter distribution of soil in each of the soil samples;
   a corrosion measurement step of taking electrochemical measurements at a plurality of soil moisture percentage values on an electrode containing the metallic material buried in each of the soil samples;
   a soil classification step of classifying the soil in each of the soil samples into a plurality of types based on the particle diameter distribution and calculating class proportions of the plurality of types;
   a corrosion rate calculation step of calculating a corrosion rate regarding each of the soil samples at each of the soil moisture percentage values based on polarization resistance measured in the electrochemical measurements and identifying a local maximum corrosion rate at which the corrosion rate is maximized;
   a corrosion estimation curve generation step of generating a corrosion estimation curve for use to estimate the corrosion amount of the metallic material using the class proportions and the local maximum corrosion rate regarding each of the soil samples; and
   a corrosion amount estimation step of acquiring the class proportions of actual soil in which the metallic material is buried, acquiring the local maximum corrosion rate corresponding to the class proportions from the corrosion estimation curve, and estimating the corrosion amount of the metallic material using the local maximum corrosion rate and a period during which the metallic material is buried in the actual soil.

2. The corrosion amount estimation method according to claim 1, wherein after adding water to each of the soil samples until the soil sample saturates, the corrosion measurement step carries out electrochemical measurements at the plurality of soil moisture percentage values by gradually reducing soil moisture percentage.

* * * * *